United States Patent [19]
Goldstein

[11] Patent Number: 5,280,273
[45] Date of Patent: Jan. 18, 1994

[54] TOXIC GAS DETECTOR SYSTEM HAVING CONVENIENT BATTERY AND SENSOR REPLACEMENT

[76] Inventor: Mark K. Goldstein, 2500 Torrey Pines Rd., La Jolla, Calif. 92037

[21] Appl. No.: 994,204

[22] Filed: Dec. 21, 1992

[51] Int. Cl.$^5$ ............................................. G08B 17/10
[52] U.S. Cl. ................................... 340/632; 340/693; 340/628; 429/96; 429/99
[58] Field of Search ............... 340/632, 633, 634, 628, 340/629, 630, 693; 429/96, 97, 98, 99, 100; 381/69; 436/169

[56] References Cited
U.S. PATENT DOCUMENTS

| | | | |
|---|---|---|---|
| 4,152,551 | 5/1979 | Hiller | 381/69 |
| 4,959,640 | 9/1990 | Hall | 340/693 |
| 5,063,164 | 11/1991 | Goldstein | 436/169 |

*Primary Examiner*—Jeffrey Hofsass
*Attorney, Agent, or Firm*—Frank D. Gilliam

[57] ABSTRACT

A detector system for sensing the presence of a toxic gas, such as carbon monoxide, and sounding an alarm. The presence of the gas is detected by passing light through a biomimetric sensing material that darkens in the presence of the gas. The system includes a housing containing a light emitter, a light detector and a mechanism for sounding an alarm. The sensing material is contained in a cell, which, together with a battery to power the system, are mounted in a drawer insertable into the housing, which has openings permitting ambient air to reach the sensing material. When fully inserted, the drawer positions the cell between the emitter and detector and brings battery contacts into connection with contacts for the light emitter and alarm. Both the battery and sensing material must be replaced periodically, typically about once every three years. The drawer is configured so that it cannot be inserted without a battery in place. Both the battery and cell are easily replaced in the drawer. A microporous filter is preferably placed between the cell and ambient air to prevent contamination by large airborne particles.

13 Claims, 3 Drawing Sheets

TOXIC GAS DETECTOR SYSTEM HAVING CONVENIENT BATTERY AND SENSOR REPLACEMENT

BACKGROUND OF THE INVENTION

This invention relates in general to sensors for toxic gases and, more particularly, to a detector system for toxic gases permitting convenient, reliable, replacement of a battery and gas sensor in a housing containing the system.

Airborne toxic gases and vapors, such as carbon monoxide, mercury, ethylene oxide, volatile organic compounds, hydrogen sulfide, etc. are difficult to detect, especially where they are odorless or present at levels that cannot be smelled or are masked by other odors. The danger of these is becoming increasingly apparent, especially in industrial plants, mines, well-sealed homes and office buildings, recreational and other vehicles and other environments in which people are present for long periods.

Recently, a solid-state biomimetric sensor has been developed by the inventor of the present application which has an extended useful life and which mimics the human response to various toxic gases and vapors. As described in U.S. Pat. No. 5,063,164 this sensor comprises a porous, semi-transparent substrate with a self-regenerating chemical sensing reagent impregnated into the substrate. The optical density of the chemical sensor changes in response to contact with the toxin. This patent describes a variety of sensing reagents and substrates. Some perform at optimum levels under high humidity conditions, while others require low humidity for optimum performance.

The sensor has a relatively long useful lifetime, typically about three years, approximately equivalent to the useful life of typical alkaline battery.

Other gas sensing compositions have been developed, such as those described by Shuler et al in U.S. Pat. 4,043,934. The disclosed sensing reagents effective with certain gases, such as reducing gases like carbon monoxide, producing a color change upon exposure. These materials, however, tend to have a short useful life, typically 2–4 months.

In order to apply these toxic gas sensor materials in practical applications, such as home or recreational vehicle use, compact, reliable, easily serviced sensing and alarm systems are needed. The system must provide accurate and reliable detection of optical transmission characteristics and/or color changes. Characteristics of certain sensor materials, such as variable response depending on ambient humidity, must be accommodated. Ease of servicing, e.g., replacement of the sensing material and battery, battery pack or main power supply, assurance that a battery or power supply is in place, is an important consideration where unskilled persons are maintaining the system.

It is, therefore, an object of this invention to provide a simple and reliable system for detecting toxic gases. Another object is to a provide system which is easily serviced to replace the sensor and battery at appropriate intervals and prevents the use of the system without a battery in place. A further object is to provide a system which can accommodate sensing materials of different types, e.g., color change, optical density change and different humidity sensitivity.

SUMMARY OF THE INVENTION

The above-noted objects, and others, are accomplished in accordance with this invention by a toxic gas detector system that basically includes a housing having openings through which ambient gases can easily pass, spaced light emitting and detecting means, an alarm responsive to changes in light received at the detector and a drawer carrying a toxic gas detection cell and battery insertable into the housing. Cooperating electrical contacts on the drawer and housing to connect the battery to the alarm and light emitter. When the drawer is fully inserted into the housing the cell is positioned between the light emitter and detector so that emitted light passes directly through the cell to the detector.

Any suitable toxic gas detecting cell may be used, using any suitable detection material. Typical toxic gas responsive reagents are described in U.S. Pat. Nos. 4,043,934 and 5,063,164, discussed above. Where the cell changes optical density in response to exposure to a toxic gas, the detector should be responsive to the same light frequency as emitted by the emitter, responding to changes in light intensity. Where the cell changes optical properties by absorbing photons in specific regions of the spectra e.g. a change in color in response to toxic gas exposure, the detector could be responsive to the emitter light color (photons with a specific band) and respond to decrease in light (on photons in that band) of that color when the cell color changes, or could be responsive to the changed color, responding to increases in toxic gas caused changes to that color. The light may include photons which are not in the visible spectrum such as in the near infra-red photons.

In order to assure that the drawer is not inserted into the housing without a battery in place, means are preferably provided to prevent insertion of an empty drawer. Also, a releasable latch to hold the drawer in the fully inserted position with the cell properly aligned with the emitter and detector is preferably provided.

In order to prevent contamination of the sensor with airborne solid particles, such as smoke particles, it is preferred that a microporous filter be provided between the cell and the air-admitting opening in the housing.

BRIEF DESCRIPTION OF THE DRAWING

Details of the invention, and of certain preferred embodiments thereof, will be further understood upon reference to the drawing, wherein.

DETAILED DESCRIPTION OF PREFERRED EMBODIMENTS

Figure 1:
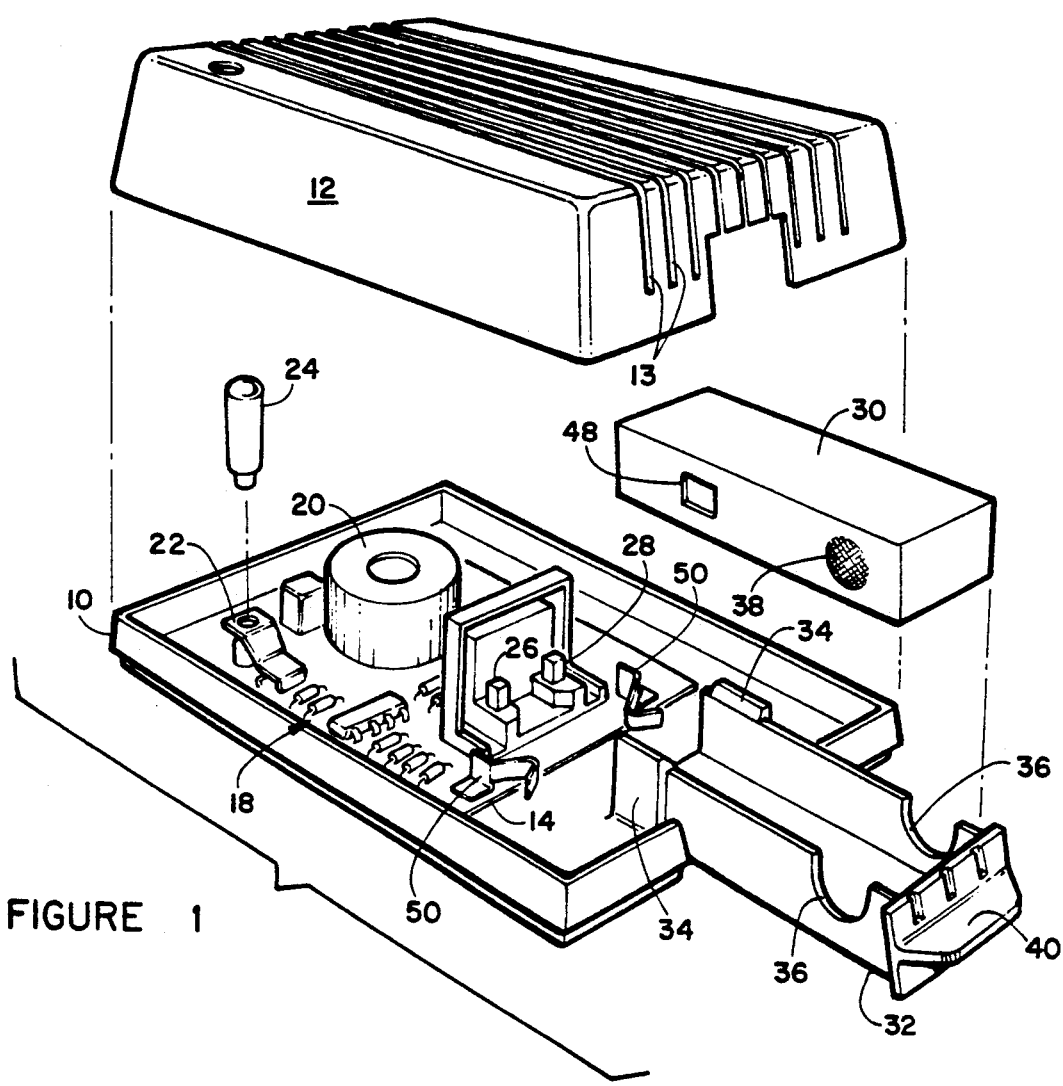
FIG. 1 is a schematic exploded perspective view showing the overall toxic gas detector.

Referring now to FIG. 1, there is seen a housing made up of a base 10 and cover 12. Cover 12 has a plurality of slots 13 that permit ambient air to circulate through the housing. A circuit board 14 mounted on base 10 carries a sensor reader assembly 16 and conventional electronic components 18 that actuate an alarm 29. The system may also include a conventional low battery alarm which sounds when battery voltage drops below a predetermined level. The electronics are conventional, available from a number of manufacturers and are of the sort used in commercial smoke alarms. Any electronic circuit capable of assessing a change in light level received at a light detector and activating an alarm may be used. Typical of such systems are those available from the BRK Electronics under the First Alert model designation No. 86RAC.

Alarm 20 may be any suitable attention-getting device, such as a buzzer, chime, bell, flashing light or the like. In order to test the battery and alarm, a manual switch 22 actuated by a push button 24 extending through cover 12 is provided.

The sensor reader assembly includes a light emitter 26 and a light detector 28. As detailed below, light from emitter 26 passes through a sensor cell to detector 28. Changes in light characteristics, e.g. photon intensity or color (spectral shift in photon absorbance), will activate alarm 20 when a sensitivity threshold is exceeded. Any suitable emitter and detector may be used. Typically, a selected band of visible or infrared light is used. Emitter 26 may conveniently be a light emitting diode and detector 28 may be a photo diode.

A box 30 containing a battery to power the system and a cell containing the toxic gas sensing material is housed in a drawer 32 for easy insertion into and removal from the housing. Guides 34 are provided on base 10 to guide drawer 32 into the proper position. Notches 36 are provided in drawer 32 to cooperate with roughened areas 38 on box 30 to permit easy removal and insertion of box 30 into drawer 32. Handle 40 on the end of drawer 32 is gripped when sliding the drawer into and out of the housing.

Figure 2:
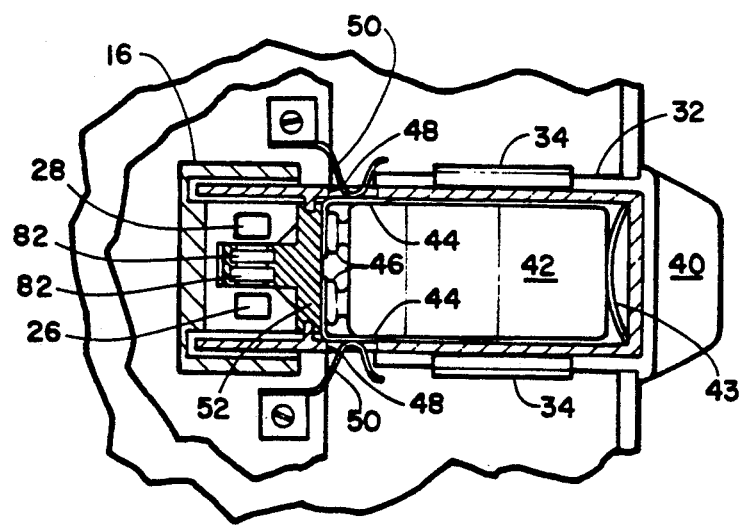
FIG. 2 is a detail plan view of the battery/sensor drawer assembly.
Figure 3:
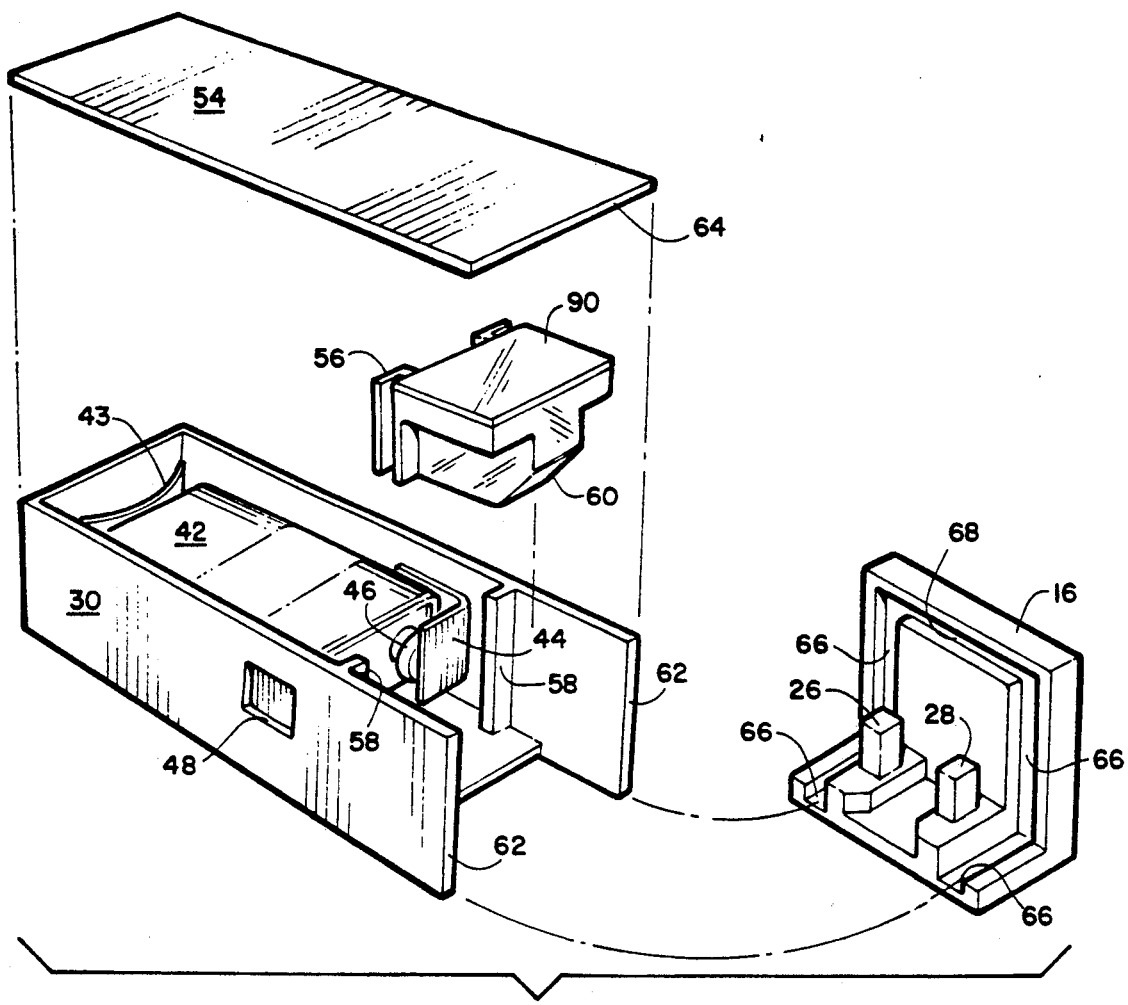
FIG. 3 is an exploded perspective view of the battery/sensor drawer.

FIGS. 2 and 3 show details of box 30 and the relationship with sensor reader assembly 16. A conventional 9 volt battery 42 is shown fitting within box 30, with contact strips 44 extending from the battery contacts 46 to a position adjacent to openings 48. Flexible spring contacts 50 on mounts 52 secured to board 14 come into contact with strip contacts 44 when drawer 32 is fully inserted and direct power to the electronic components 18. A spring strip 43 maintains battery contacts 46 in tight engagement with contact strips 44. Any other suitable battery, with appropriately configured contact strips 44 to connect to flexible strips 50 may be used as desired.

Sensor housing 52 is removable mounted in box 30 and covered by box lid 54 when in use, with a space between the top of housing 52 and the underside of lid 54. Lid 54 may be releasably held in place by any suitable means, such as tacky adhesives, hook-and-loop material, conventional clips, tape, a groove around the upper pox edge into which the lid snaps, or the like.

Sensor housing 52 is formed from any suitable material that transmits the light wavelengths being used. Many conventional transparent plastics are suitable. Housing 52 has guides 56 that slide over ridges 58 on box 30. Alternatively, housing could carry vertical ridges to slide into grooves in box 30 replacing box ridges 58. The sensor material is carried in the lower, narrow portion 60 of housing 52. When drawer 32 is fully inserted into the housing base 10, the side edges 62 of box 30 and the front edge of lid 54 enter grooves 66 and 68, respectively, in sensor reader assembly 16 as schematically indicated in FIG. 3. Lower portion 60 of sensor housing 52 enters between emitter 26 and detector 28 and is precisely positioned with the sensor material therebetween.

Figure 4:
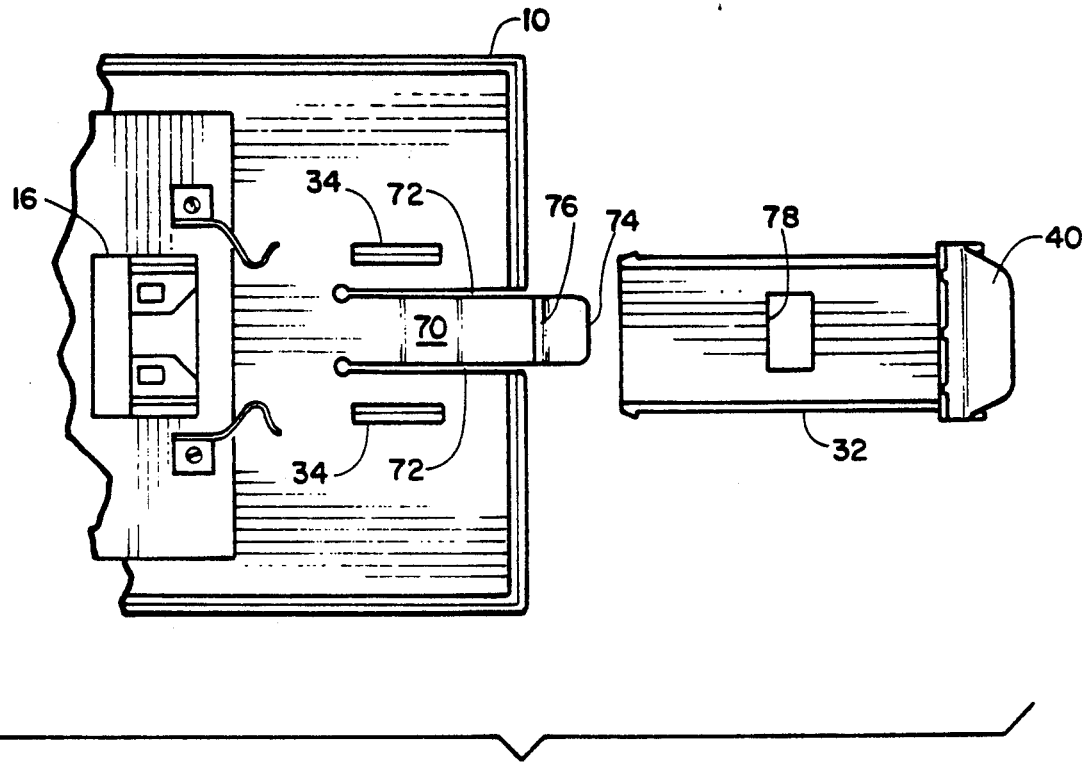
FIG. 4 is a detail plan view of the drawer and latching components.
Figure 5:
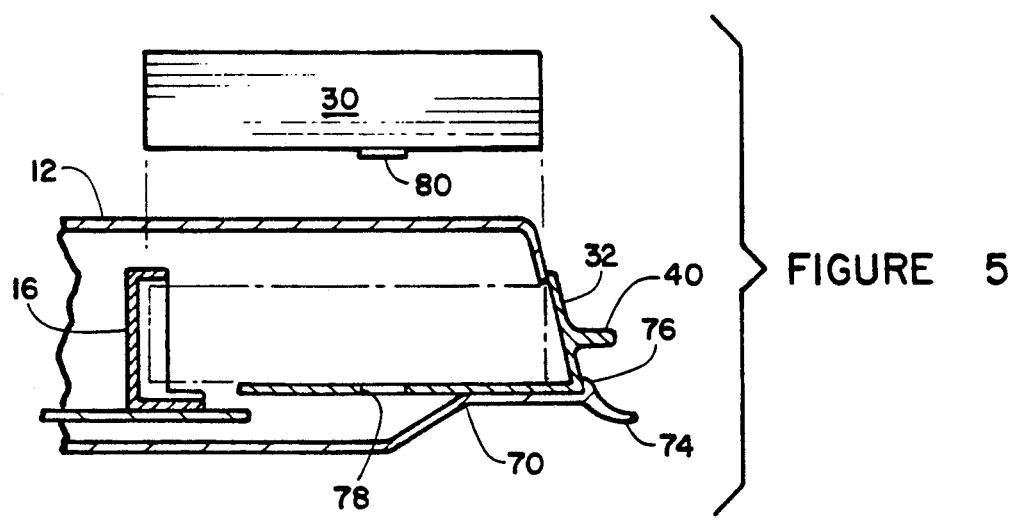
FIG. 5 is a section view of the drawer and latching components, take on line 5—5 in FIG. 4.

FIGS. 4 and 5 show the preferred mechanisms for preventing insertion of drawer 32 without a battery in place and for releasably securing the drawer in the fully inserted position. A spring finger 70 is created by cutting two slots 72 in the bottom of base 10, which is formed from a reasonably stiff plastic material. As seen in FIG. 4, the end portion of finger is bent upwardly slightly to clear any wall, ceiling or other structure to which base 10 might be fastened. While finger 70 is biased to a straight position approximately coplanar with the bottom of base 10, by pressing downwardly on lip 74 finger 70 can be bent away.

Finger 70 includes a low upstanding, precisely located, ridge 76. When drawer 32 is to be inserted, lip 74 is pushed down so that the forward end of the drawer passes over ridge, then lip 74 is released and the drawer is pushed fully into the housing. However, if a battery box 30 is not in place in drawer 32, ridge 76 will enter hole 78 in the bottom of the drawer, preventing further insertion. Battery box 30 includes a small plate 80 on the bottom that precisely fits hole 78 when the battery box is in place. Then, ridge will slide past hole 76 which is filled with plate 80. When drawer 32 is fully inserted, ridge 76 will snap up over the lower outer edge of the drawer and hold it in place against accidental withdrawal. This is important, since even a slight withdrawal could move the sensor material out of the path between emitter 26 and detector 28. To remove drawer 32, lip 74 is simply pushed downwardly and the drawer is pulled out by handle 40

Figure 6:
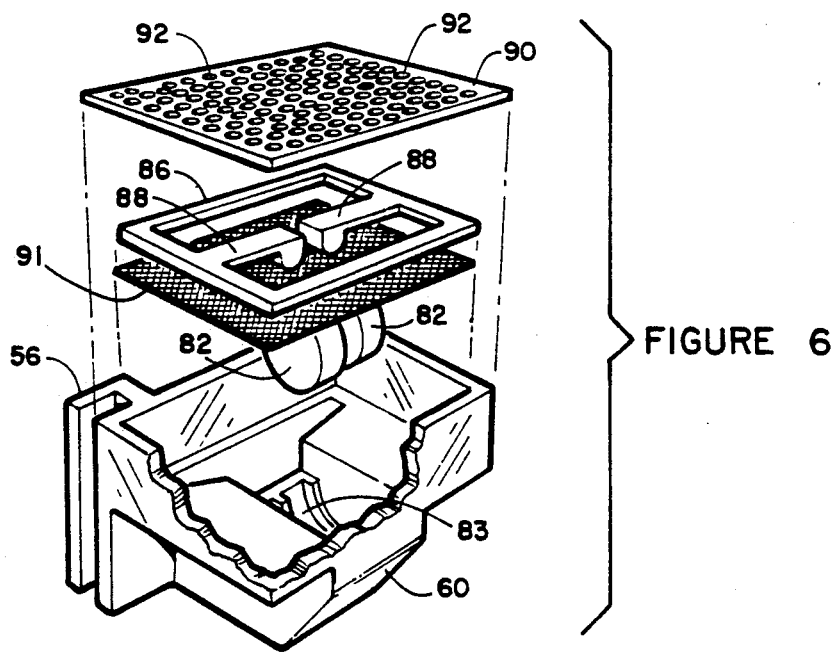
FIG. 6 is an exploded perspective view of the sensor assembly.

Details of a preferred sensor housing 54 and internal components are provided in FIG. 6. Cells 82 containing material responsive to toxic gases are supported in the narrow lower portion 60 of housing 54. Any suitable sensing material may be used. Typical such materials include the biomimetic materials detailed in my U.S. Pat. No. 5,063,164. Some sensing materials are more effective at high humidity levels, while others are better with low humidity. In those cases it is preferred to include two cells 82 in series, each containing one of the different materials. Disk shaped cells 82 are preferred, fitting into correspondingly shaped channels 83. The channels may have a spring side, or be made from flexible material, if desired, to permit disks of somewhat varying diameter to be used.

Since some sensitive materials can be contaminated by contact with airborne particles, it is preferred that a sheet of microporous filter material 84 be placed in the path of air reaching the sensor cells 82. Any suitable filter material can be used. Typical filter materials 91 can be obtained under the trademarks Gortex, Tyvek and Milpore. A frame 86 holds the filter material in place. A pair of spring arms 88 hold cells 82 in channels 83. A cover 90, having a plurality of perforations 92 through which air can pass is secured to housing 52 by any suitable means, such as a releasable adhesive.

Other applications, variations and ramifications of this invention will occur to those skilled in the art upon reading this disclosure. Those are intended to be included within the scope of this invention, as defined in the appended claims.

I claim:

1. A toxic gas detector system which comprises:
   a housing having openings permitting ambient gases to pass therethrough;

a drawer removably insertable into said housing;

said drawer adapted to carry a battery and a toxic gas detection cell which changes light transmission characteristics when exposed to a selected toxic gas;

said cell positioned in said drawer to permit light to pass through said cell and drawer from one side of the cell to the other;

light emitting means and light detecting means in said housing positioned to direct said light from said emitter to said detector through said cell when said drawer is fully inserted in said housing;

means for sounding an alarm when light transmission through said cell changes; and contact means between said drawer and housing whereby said battery is electrically connected to said alarm means and light emitter when said drawer is fully inserted in said housing.

2. The toxic gas detector system according to claim 1 further including a box for enclosing said battery and cell, said box removably insertable in said drawer, and means for preventing full insertion of said drawer into said housing without said box in place.

3. The toxic gas detector system according to claim 2 wherein said housing includes a spring finger including a ridge biased toward said drawer, said drawer having a hole which encounters said ridge when said drawer is partially inserted into said housing and said box bears a plate which fills said hole when said box is in said drawer, so that said ridge enters said hole and prevents further insertion of said drawer only when said box is not in said drawer.

4. The toxic gas detector system according to claim 3 wherein said ridge engages an outer edge of said drawer when fully inserted in said housing preventing removal of said drawer and said finger includes release means for releasing said ridge from said edge to permit withdrawal of said drawer.

5. The toxic gas detector system according to claim 2 further including first electrical contacts on said battery box adapted to be in electrical connection with contacts on a battery in said box and second electrical contacts in said housing adapted to engage said first contacts when said drawer is fully inserted into said housing and direct power to said alarm sounding means.

6. The toxic gas detector system according to claim 2 wherein said cell is mounted in a housing carried by said box in said drawer, and includes filter means for preventing airborne contaminates from reaching said cells.

7. The toxic gas detector system according to claim 6 wherein said housing is adapted to contain plural disk-shaped cells mounted in series in circular channels, said housing including spring arms for holding cells in said channels, whereby plural cells being sensitive under different conditions can be accommodated.

8. A toxic gas detector system which comprises:

a housing having openings permitting ambient gases to pass therethrough;

a drawer removably insertable into said housing;

said drawer adapted to carry a box holding a battery and a toxic gas detection cell which changes light transmission characteristics when exposed to a selected toxic gas;

means for preventing full insertion of said drawer into said housing, without said box in said drawer and for releasably holding said drawer in the fully inserted position;

said cell positioned in said drawer to permit light to pass through said cell and drawer from one side of the cell to the other;

light emitting means and light detecting means in said housing positioned to direct said light from said emitter to said detector through said cell when said drawer is full inserted in said housing;

means for sounding an alarm when light transmission through said cell changes; and contact means between said drawer and housing whereby said battery is electrically connected to said alarm means and light emitter when said drawer is fully inserted in said housing.

9. The toxic gas detector system according to claim 8 wherein said means for preventing full insertion of said drawer without said box includes a spring finger on said housing which includes a ridge biased toward said drawer, said drawer having a hole which encounters said ridge when said drawer is partially inserted into said housing and said box bears a plate which fills said hole when said box is in said drawer, so that said ridge enters said hole and prevents further insertion of said drawer only when said box is not in said drawer.

10. The toxic gas detector system according to claim 9 wherein said ridge engages an outer edge of said drawer when fully inserted in said housing preventing removal of said drawer and said finger includes release means for releasing said ridge from said edge to permit withdrawal of said drawer.

11. The toxic gas detector system according to claim 8 further including first electrical contacts on said battery box adapted to be in electrical connection with contacts on a battery in said box and second electrical contacts in said housing adapted to engage said first contacts when said drawer is fully inserted into said housing and direct power to said alarm sounding means.

12. The toxic gas detector system according to claim 8 wherein said housing includes filter means for preventing airborne contaminates from reaching said cells.

13. The toxic gas detector system according to claim 12 wherein said cell housing is adapted to contain plural disk-shaped cells mounted in series in circular channels, said housing including spring arms for holding cells in said channels, whereby plural cells being sensitive under different conditions can be accommodated.

* * * * *